(12) United States Patent
Luther et al.

(10) Patent No.: US 6,890,321 B2
(45) Date of Patent: May 10, 2005

(54) HARD TIP OVER-THE-NEEDLE INTRAVENOUS CATHETER

(76) Inventors: Ronald B. Luther, 530 Kings Rd., Newport Beach, CA (US) 92663; Charles W. Dickerson, 17651 Amaganset Way, Tustin, CA (US) 92780; James I. Wright, 2521 N. Brynwood St., Santa Ana, CA (US) 92705

( * ) Notice: Subject to any disclaimer, the term of this patent is extended or adjusted under 35 U.S.C. 154(b) by 37 days.

(21) Appl. No.: 10/644,047

(22) Filed: Aug. 19, 2003

(65) Prior Publication Data

US 2004/0073170 A1 Apr. 15, 2004

Related U.S. Application Data

(63) Continuation of application No. 09/524,039, filed on Mar. 13, 2000, now abandoned.

(51) Int. Cl.$^7$ ............................................... A61B 1/08
(52) U.S. Cl. ................................................ 604/164.01
(58) Field of Search ..................... 604/164.01, 164.02, 604/164.03, 164.04, 164.05, 164.06, 164.07, 164.08, 164.09, 173, 44, 158, 172

(56) References Cited

U.S. PATENT DOCUMENTS

| | | | |
|---|---|---|---|
| 4,762,516 A | | 8/1988 | Luther et al. |
| 4,841,007 A | * | 6/1989 | Zdrahala et al. ............... 528/28 |
| 4,935,480 A | * | 6/1990 | Zdrahala et al. ............... 528/28 |
| 5,531,701 A | | 7/1996 | Luther |
| 5,683,370 A | * | 11/1997 | Luther et al. ................ 604/528 |
| 5,830,190 A | * | 11/1998 | Howell ................... 604/168.01 |
| 5,913,848 A | * | 6/1999 | Luther et al. ................ 604/524 |
| 5,916,208 A | * | 6/1999 | Luther et al. ................ 604/508 |
| 5,957,893 A | * | 9/1999 | Luther et al. ........... 604/164.01 |

* cited by examiner

*Primary Examiner*—Daniel Robinson
(74) *Attorney, Agent, or Firm*—Knobbe, Martens, Olson & Bear, LLP

(57) ABSTRACT

A soft over-the-needle (OTN) catheter that has been treated at a distal end to provide a higher durometer (i.e., harder) surface to facilitate insertion of the catheter into a patient is provided. The catheter preferably comprises a soft flexible tube made of polyurethane and having a hardness in the range of 50A to 90A where the treated distal end has a hardness of above 90A. The OTN catheter may also include an annular abutment shoulder formed at a distance from the distal end of the catheter. An insertion needle also comprises an abutment means, preferably a collar positioned on the exterior of the insertion needle, to abut the abutment shoulder of the catheter. Where the catheter is to be fed significantly into the vascular system, an optional metal ring may be secured within the catheter, adjacent the internal shoulder. When the needle is removed, the metal ring remains in place, permitting electromagnetic tracking of the catheter as it is fed through the vascular system. In an alternative embodiment, rather than chemically treating the distal end of a soft catheter, a discrete segment of hard tubing is press fit into the interior of the distal end of a soft catheter.

20 Claims, 1 Drawing Sheet

HARD TIP OVER-THE-NEEDLE INTRAVENOUS CATHETER

RELATED APPLICATION

This application is a continuation of U.S. patent application Ser. No. 09/524,039 filed on Mar. 13, 2000, now abandoned, the disclosure are hereby incorporated in its entirety herein by reference.

BACKGROUND OF THE INVENTION

1. Field of the Invention

The present invention relates generally to catheters used in the treatment of patients and, more particularly, to soft over-the-needle intravenous catheters that have been treated to harden the distal end to reduce the risk of vascular trauma to the patient and to minimize discomfort during use.

2. Description of the Related Art

Intravenous catheters are well known in the art and serve the function of withdrawing fluids from, or delivering fluids to, a patient undergoing treatment. Typically, either a through-the-needle or an over-the-needle catheter is inserted percutaneously using an insertion needle. With the former catheter, the insertion needle includes a lumen through which the catheter is inserted. With the latter, the needle is inserted into the lumen within the catheter, whereby the catheter fits snugly around the needle. In either case, after the needle and catheter are inserted into the patient's vascular system, the needle is withdrawn, leaving the catheter in place.

Conventional catheters are made of a relatively hard thermoplastic material, such as polyvinylchloride, Teflon® polyurethane or the like, which provides stiff columnar strength during insertion. While the catheter may exhibit axial flexibility, the stiffness of the catheter walls ensures that the catheter will not collapse and will readily follow the needle into the patient's vascular system. The problem with these relatively hard catheters, however, is that they often cause vascular trauma when in use. For example, when the catheter is inserted into the vascular system, the stiffness of the catheter resists the tendency of the blood flow to move the catheter away from the vessel wall and toward the center of the vessel. As such, as the clinician advances the catheter further into the patient, the distal end of the catheter has a tendency to scrape along the wall of the blood vessel as it bends to conform to the shape of the vessel as will be understood by those of skill in the art. Moreover, where the catheter is fed significantly through the patient's vascular system, the catheter's stiffness leads to uncontrolled contact with the vessel wall at various locations, causing discomfort to the patient.

More recently, there have been efforts to employ a softer catheter, one made with a material that is more resilient and flexible and less resistant to the force of blood flow within the blood vessel. Such catheters are beneficial in that they reduce discomfort to the patient and decrease significantly the potential for damage to the blood vessel walls. A limitation of soft material catheters, however, is that they are more difficult to insert than the relatively hard catheters. Due to the resistance of the patient's skin and muscle tissue during insertion, the distal end of the soft catheter often either rolls up axially away from the distal end and/or wrinkles proximally in an accordion-like fashion. Under those circumstances, the catheter does not effectively enter the vascular system on the first attempt, requiring repeated efforts at reentry, which is discomforting to the patient and frustrating to the clinician.

There is a need, therefore, to overcome the limitation of soft material catheters so that they are more effective yet avoid discomfort to the patient by repeated reentry attempts.

SUMMARY OF THE INVENTION

The present invention comprises a soft over-the-needle (OTN) catheter that has been treated at a distal end to provide a higher durometer (i.e., harder) surface to facilitate insertion of the soft catheter into the vascular system of a patient. The invention further comprises an insertion needle for use with the OTN catheter. The catheter preferably comprises a soft flexible tube made of polyurethane and having a hardness in the range of 50 A to 90 A. A soft material catheter contemplated by the present invention is described, for example, in co-pending application, Ser. No. 09/146,451, which is incorporated in its entirety herein by reference.

In one embodiment, the OTN catheter is chemically treated by dipping the distal end of the catheter into a liquid solution of harder thermoplastic material that, when dry, exhibits a hardness greater than that of the underlying catheter material. The portion of the catheter treated, therefore, is stiffer than it would be if untreated. With a stiffer distal end, the step of advancing the OTN catheter with the insertion needle into the patient results in the catheter more closely following the needle into the patient's vascular system, as normally occurs with conventional relatively hard catheters. No rolling up or accordion-like wrinkling results. Moreover, because only the tip of the catheter is treated, the majority of the catheter remains soft, reducing the discomfort of the patient when the catheter resides in the vessel. Given the soft, highly flexible nature of the untreated portion of the catheter, the blood flow through the vessel tends to push the hardened tip of the catheter away from the vessel wall and toward the center of the vessel, the area of highest velocity flow, sometimes referred to as the hemodynamic center. The result is that there is less risk of the catheter scraping the vessel wall as the catheter is advanced.

In the preferred embodiment, an abutment means is also provided wherein, for example, the interior surface of the treated distal end of the OTN catheter includes an annular abutment shoulder formed at a distance from the distal end of the catheter. The preferred embodiment also comprises a corresponding abutment on the insertion needle configured to engage the abutment shoulder of the catheter, preferably a collar positioned on the exterior of the insertion needle spaced at a distance from the distal tip of the needle. The collar is configured to engage the interior catheter shoulder when the needle is inserted into the catheter. By engaging the shoulder, the insertion needle further assists in advancing the treated soft catheter into the vascular system as the needle is pushed into the patient. Where the catheter is to be fed significantly into the vascular system, an optional metal ring may be secured within the catheter, preferably adjacent the internal shoulder, so that the needle collar engages the metal ring during insertion. When the needle is removed, the metal ring remains in place, permitting tracking of the catheter as it is fed through the vascular system. It is contemplated that means for detecting metal would be used to track the metal ring and, thus, the catheter as it is advanced.

In an alternative embodiment, rather than chemically treating the end of a soft catheter, a discrete segment of hard tubing is press fit into the interior of the distal end of a soft catheter. The soft tubing catheter is heated to expand sufficiently to permit insertion of a short segment of hard material tubing into one end of the soft tubing. When the soft tubing catheter cools, it contracts to tightly surround the hard tubing, making the soft catheter end stiffer than without the inserted segment. An insertion needle with a collar may be used so that the collar engages the proximal end of the hard interior tubing so as to assist in inserting the catheter into the patient's vascular system. In the alternative, an insertion needle with a tapered exterior diameter to tightly engage the interior surface of the hard tubing may also be used to insert the catheter with hard tubing segment.

BRIEF DESCRIPTION OF THE DRAWINGS

These and other features and advantages of the invention will now be described with reference to the drawings, which are intended to illustrate and not to limit the invention.

DETAILED DESCRIPTION OF THE PREFERRED EMBODIMENTS

Figure 1:
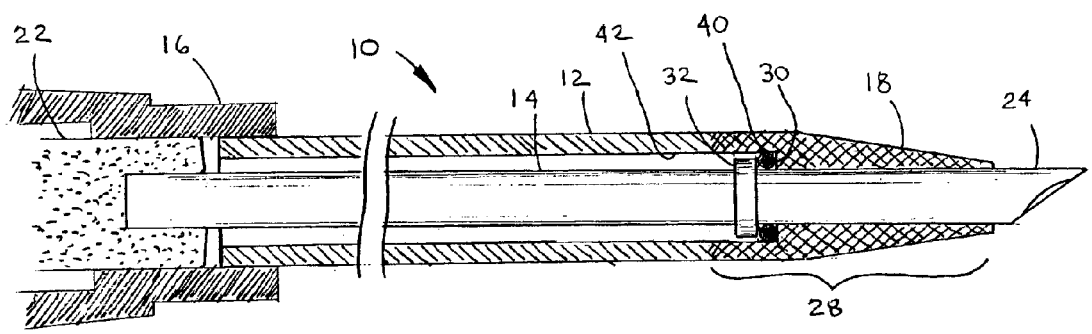
FIG. 1 is a cross-sectional view of the preferred embodiment of the present invention.
Figure 2:
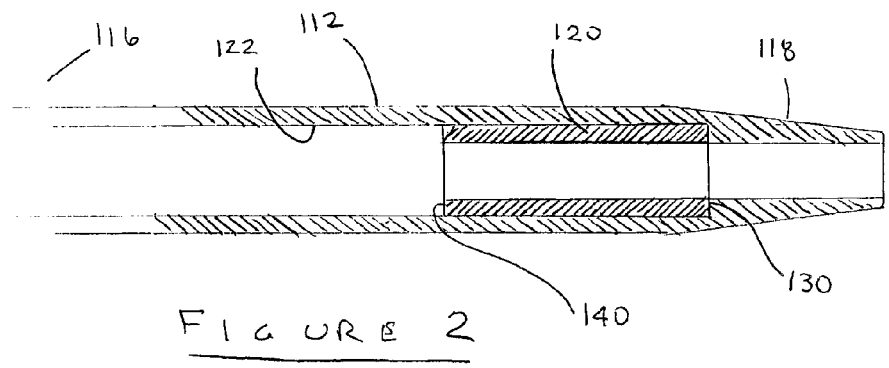
FIG. 2 is a cross-sectional view of an alternative embodiment of the present invention.

Reference may now be made to FIGS. 1 through 2 where the invention may be described in greater detail. With specific reference to FIG. 1, the present invention is a catheter assembly 10 comprising an over-the needle (OTN) catheter 12 and an insertion needle 14. The OTN catheter 12 comprises a length of flexible tubing having a lumen therethrough wherein the tubing is made preferably of a soft thermoplastic material such as polyurethane. The polyurethane tubing preferably has a hardness ranging between 50 and 90 on the Shore A scale, more preferably in the range between 65 A and 85 A. The soft resilient material serves to reduce vascular trauma and discomfort when in use as will be understood in the art. A suitable polyurethane is sold under the tradename Carbothane™ by Thermedics Corporation of Woburn, Mass. It should be recognized that other thermoplastic materials may be used that are soft and resilient and that would be effective at minimizing vascular trauma when being inserted into or residing within a patient's vascular system.

The catheter 12 has a proximal end comprising a hub or fitting 16 and a distal, preferably tapered, end 18, wherein the distal end is the leading end inserted into the patient along with the insertion needle 14. The insertion needle 14 has a proximal end comprising a fitting 22, configured to permit a clinician to safely handle the needle, and a tapered distal end 24 terminating in a sharp point used to pierce a patient's skin and vascular system. The fitting 22 of the insertion needle 14 preferably has a configuration suitable for residing within the fitting 16 on the catheter during catheter insertion. The catheter fitting 16 also preferably comprises a female luer opening with a flange (not shown) for engagement with a fluid supply line having a corresponding Luer or Luer Lock. Such locking elements are well known in the art.

Preferably, the catheter assembly 10 is supplied to a clinician with the insertion needle 14 already inserted through the lumen in the catheter 12, wherein the exposed tip of the needle and the catheter 12 are enclosed within a protective sheath (not shown). The assembly 10 may, therefore, be easily handled until it is desired to use the assembly. The catheter assembly also preferably includes a guard means for covering the exposed tip of the needle after the needle has been retracted from the patient following catheter insertion. As has been addressed in the prior art, an exposed needle tip creates a problem for the clinician, particularly given the health hazards to clinicians associated with exposure to blood drawn from patients. Numerous means have been developed to automatically ensheathe the tip as the needle is withdrawn from the catheter. An example of such means is the needle tip guard sold by B. Braun Medical Inc. under the trade name Introcan®. Another example is manufactured by Johnson & Johnson and is described in U.S. Pat. No. 4,762,516 to Luther. A method of using the present invention preferably includes the step of providing a guard means that locks into place protecting the needle tip during retraction, as discussed below.

In the preferred embodiment, the distal end 18 of the OTN catheter has been treated via one of several hardening methods, preferably a chemical treatment method, some of which are described further below. As explained above, treating the distal end 18 of the OTN catheter so as to make it stiffer makes it easier to insert the catheter into a patient undergoing treatment. The stiffer end resists rolling up or accordion like scrunching during insertion of the catheter into the patient. Preferably, the polyurethane catheter 12 has been treated with a hard thermoplastic material such that the resulting treated distal end of the catheter 12 has a hardness above 90 on the Shore A scale and, more preferably, a hardness of 99 on the Shore A scale. The extent of treatment is represented by brace 28, the length of which may be user specified. A soft catheter 12 having at least inches of treatment is effective. However, any length of the distal end of the catheter may be so treated as will be easily understood by those skilled in the art.

The present invention catheter system may also comprise abutment means for further facilitating advancement of a soft material OTN catheter. In one embodiment, the abutment means comprises an abutment shoulder 30 integral with the interior of the catheter 12 and an external collar 32 secured to the insertion needle 14. The shoulder 30 and the collar 32 are positioned at a distance from the distal end of the catheter and needle, respectively. In one embodiment, when the needle 14 is fully inserted through the catheter 12, the collar 32 advantageously abuts the interior shoulder 30 to provide leverage in advancing the catheter into the patient during insertion. The collar 32 is preferably positioned on the needle 14 such that it abuts the shoulder when a sufficient portion of the distal end 24 of the needle extends beyond the distal end 18 of the catheter. This leaves the tip of the needle exposed for insertion into the patient. Other embodiments of the abutment means are contemplated by the present invention, such as that described in U.S. Pat. No. 5,531,701 to Luther, which is incorporated in its entirety herein by reference. Moreover, the interior abutment shoulder of the catheter need not be a sharp or angled corner, as illustrated in FIG. 1, but may be a smooth, less dramatic, transition from a proximal lumen diameter to a smaller distal lumen diameter. Such an arrangement would preferably permit engagement with a complimentary abutment feature on the insertion needle. Other arrangements of abutments may be used so long as they are effective at transferring insertion forces from the needle to the catheter.

Where it is desired to feed the soft material catheter well into the vascular system of the patient and to track the advancement of the catheter during the process, a metal ring 40 may be securely positioned within the lumen 42 of the catheter 12. Preferably, the metal ring 40 is sized and configured to sit adjacent the interior shoulder 30 within the catheter 12 in a secure position, although a metal ring may be used even where an interior shoulder 30 is not provided. Preferably, the metal ring 40 is press fit into place by, for example, heating the catheter to expand the diameter of the interior lumen 42 to a size larger than the outer diameter of the metal ring. While the catheter is still expanded, the ring may be inserted easily into the lumen 42 from the proximal or distal end and placed adjacent the shoulder, if provided, as shown in FIG. 1. When the catheter is cooled, the catheter wall closes tightly around the ring, securing it motionless within the catheter. A secure fit is preferred to avoid any risk of the ring becoming dislodged while in the patient. When the metal ring 40 is used, the collar 32 of the insertion needle 14 may be used to abut the metal ring 40 in a similar manner as described above so that the force exerted upon the insertion needle 14 is transferred to the metal ring 40 and to the catheter 12.

The present invention also comprises a method of using an insertion needle to insert a soft material catheter into a patient wherein the method comprises the steps of providing a catheter assembly including a catheter and an insertion needle where the catheter comprises a length of soft material tubing having a lumen extending therethrough. The method further includes the steps of treating the tip at the distal end of the catheter to stiffen the material, introducing an insertion needle through the lumen of the catheter to tightly engage the catheter, both distally and proximally, inserting the catheter assembly into the patient to penetrate the patient's vascular system, and withdrawing the needle from the catheter to permit connection of the catheter to a delivery tube for fluid communication therewith. The method may further comprise providing a catheter assembly having an abutment means for enhanced insertion of the catheter and the insertion needle, wherein said abutment means permits the transfer of at least some insertion forces from the insertion needle to the catheter to enhance effective advancement of the catheter into the patient. The present method may further comprise the step of ensheathing the needle tip with a guard means during needle retraction to protect against human contact with the needle tip after withdrawing the needle from the catheter. An alternative method comprises inserting a hard material insert into the catheter to effectively stiffen the distal end without the need to treat the catheter.

Where it is desired to do so, there are several possible methods contemplated by the present invention for hardening the distal end of a soft polyurethane catheter. Some methods involve imbibing into the catheter tip a relatively hard thermoplastic material that reacts with the existing isocyanate hard segments within the polyurethane catheter. By doing so, the ratio of hard segments to soft segments within the polymer matrix is increased, leaving the treated tip material stiffer than it was prior to treatment. Other methods involve forming an interpenetrating network polymer (IPN) in which a polymer of hard thermoplastic material is interweaved within the polymer matrix of the catheter at a molecular level. No chemical reaction actually takes place with the existing hard segments. The step of forming an IPN may comprise introducing a compound that forms an interweaving polymer in situ or it may comprise interweaving an already polymerized compound into the existing polymer matrix. The result in either case is an increase in the content of high durometer material within the treated portion of the catheter.

In one example of the first method identified above, one selects a monomer that is capable of forming a rigid polymer, e.g., monomeric hexamethylene diisocyanate, to react with the existing hard segments in the polyurethane catheter. Other diisocyanates are contemplated, including but not limited to MDI, H12MDI, IPDI, TDI and TMHDI, to react with the existing hard segments. With this method, the monomeric hexamethylene diisocyanate is introduced into a solvent, for example, tetrahydrofurane (THF). Other solvents are acceptable as long as they satisfactorily dissolve the monomer selected and also swell the polyurethane catheter when exposed to it to permit the monomer to be adequately drawn into the polymer matrix. A catalyst, such as dibutyltin dilaurate, is introduced into the solvent to catalyze the reaction between the monomer and the existing hard segment of the catheter. Other catalysts are acceptable so long as they are able to catalyze a reaction between the isocyanate groups of the monomer and the existing hard segment, respectively, including, but not limited to, salts of tin, zinc and titanium. The THF solvent dissolves the monomeric hexamethylene diisocyanate and swells the soft catheter, pulling the solvent and monomer into the interstices of the catheter matrix when the catheter is dipped into the solution. With the catalyst present, the monomeric hexamethylene diisocyanate reacts with the existing hard segments of the catheter, forming allophanate linkages, resulting in a stiffer material when dry.

In one example of the second method described above, a hardening polyurethane material is introduced into the catheter through an in situ polymerization process. A solution of monomeric hexamethylene diisocyanate and a tin catalyst, for example, are prepared using THF as a solvent. A chain extender, e.g., 1,4-butanediol, is preferably added, although other short chain diols or triols may be used. The 1,4-butanediol chain extender triggers a polymerization reaction when the soft catheter is introduced into the solution, whereby a continuous chain of polyurethane is formed in situ and interweaved with the existing hard segments. No chemical reaction with the existing hard segments is intended to occur.

In a second example of the second method, an IPN is again formed, only in this method the IPN is formed using a polyurethane polymer other than diisocyanate, preferably one that has already been polymerized. No in situ polymerization is required in this second example. The polymer may be a styrenic, an acrylate, a polycarbonate, or other rigid polyurethanes or polyurethane copolymers. As with the first example, the soft catheter is introduced into a solution of the desired polymer, a catalyst and a solvent, such as those referred to above.

In a third example of the second method of forming an IPN, a process of forming a polymer in situ is used in which the thermoplastic chosen is not a polyurethane but, rather, an acrylate, such as monomeric methyl methacrylate, which contains a peroxide or a photo-labile molecule that will initiate free radical polymerization. Other acceptable thermoplastic polymers include styrenics, polycarbonates, polyesters, epoxies or 2-part polyurethane systems.

It is contemplated that, with the methods described above, or with other effective chemical treatment methods, the material chosen to provide hardness to the catheter may be hydrophilic or hydrophobic in nature and the beneficial result described above may still be achieved. An advantage of at least some hydrophilic materials, however, is that such material will later soften after residing in the patient for an extended time, reducing even further the possibility of vascular trauma.

Other non chemical methods may also be used to treat the end of a soft material catheter so that a stiffer material results. For example, it may desired to thermally treat the distal end of a catheter to increase the hardness thereof or to treat the distal end of the catheter with radiation.

Referring to FIG. 2, an alternative embodiment of the present invention catheter system is described. In this alternative embodiment, the soft material catheter is not treated. Referring to FIG. 2, the alternative catheter assembly comprises a catheter 112 made almost entirely of soft material having a hardness in the range of 50 to 90 on the Shore A durometer scale. The catheter 112 has a proximal end 116 and a distal, preferably tapered, end 118.

The system further comprises a hard thermoplastic insert 120 within a lumen 122 in the catheter 112. The insert 120 may be inserted in a manner similar to that described above for the metal ring 40 of FIG. 1. Where a shoulder 130 is provided, the insert 120 may be press fit adjacent the shoulder 130 at or near the distal end 118 of the catheter 112. The result is that the distal end 118 of the catheter 112 is effectively stiffer than it would be otherwise. The increased resulting stiffness has the advantage of minimizing rolling up and/or accordion-like wrinkling of the soft catheter during insertion. With this alternative arrangement, the needle 14 of FIG. 1 may be used where the collar 32 is sized and configured to abut the proximal end 140 of the hard material insert 120 as it did with the metal ring 40 and the interior shoulder 30 of the embodiment of FIG. 1. By abutting the proximal end 140 of the hard insert 120, the needle may facilitate insertion into the patient while avoiding trauma to the patient or vein.

The invention may be embodied in other specific forms without departing from its spirit or essential characteristics. The described embodiment is to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed is:

1. An over-the-needle catheter assembly comprising a catheter of unitaly construction made of soft material having a lumen therethrough, said catheter material having a hardness in the range of 50 to 90 on the Shore A durometer scale, said catheter having a distal end integral with said catheter that serves as the leading end when inserted into the patient, said distal end being stiffer than the remaining portion of said catheter so as to facilitate insertion of said catheter into the patient.

2. The catheter assembly of claim 1, wherein said distal end of said catheter has been treated to a hardness that is above about 90 on the Shore A scale.

3. The catheter assembly of claim 1, wherein said distal end of said catheter has been chemically treated with a hard thermoplastic material.

4. The catheter assembly of claim 1, wherein said distal end of said catheter has been treated by radiation.

5. The catheter assembly of claim 1, further comprising an insert that is configured to be securably positioned within said distal end of said catheter to effectively stiffen said distal end of said catheter.

6. The catheter assembly of claim 1, further comprising abutment means to enhance insertion of said catheter into the patient.

7. The catheter assembly of claim 6, wherein said abutment means comprises an interior abutment spaced at a distance from said distal end of said catheter, said abutment defining a transition in the internal diameter of a lumen through said catheter.

8. The catheter assembly of claim 7, further comprising an insertion needle for inserting said catheter into a patient, wherein said abutment means further comprises an abutment on said insertion needle that is complimentary with said abutment on said catheter.

9. The catheter assembly of claim 8, wherein said catheter further comprises an interior shoulder and said insertion needle further comprises a collar secured to the exterior thereof, said shoulder and collar configured to abut when said insertion needle is directed through said lumen within said catheter.

10. The catheter assembly of claim 1, further comprising a metal ring configured to be secured within a lumen of said catheter to permit tracking of said catheter during advancement through the patient's vascular system.

11. The catheter assembly of claim 1, further comprising a guard that covers the tip of a needle when said needle is withdrawn from said catheter to protect against human contact with the needle tip.

12. A method of using an insertion needle to insert a soft material catheter into a patient comprising the steps of:

providing a catheter assembly including a catheter and an insertion needle where said catheter comprises a unitary length of soft material having a lumen extending therethrough, said catheter material having a hardness in the range of 50 to 90 on the Shore A durometer scale, treating an integral distal end of said catheter to stiffen the material at said distal end so that it resists the tendency of a patient's skin and vascular system to move said catheter proximally, introducing an insertion needle through said lumen of said catheter to assist in inserting said catheter, inserting said catheter assembly into the patient's vascular system, and withdrawing said needle from said catheter to permit connection of a proximal end of said catheter to a tube for fluid communication therewith.

13. The method of claim 12, further comprising the step of providing an abutment means for distal engagement between said catheter and said insertion needle, wherein said abutment means permits the transfer of at least some insertion forces from said insertion needle to said catheter to enhance effective advancement of said catheter into the patient.

14. The method of claim 13, wherein said abutment means comprises an internal abutment in said lumen of said catheter spaced at a distance from said distal end of said catheter, said abutment defining a transition in the diameter of said lumen.

15. The method of claim 14, wherein said abutment further comprises an abutment on the exterior of said insertion needle configured to abut the abutment of said catheter during the step of inserting the catheter assembly into the patient.

16. The method of claim 12, further comprising the step of providing a guard that covers a tip of said needle when said needle is withdrawn from said catheter to protect against human contact with said needle tip.

17. The method of claim 12, wherein the step of treating a distal end of said catheter comprises inserting a hard material insert into said distal end.

18. The method of claim 12, wherein the step of treating a distal end of said catheter comprises chemically adding a hard thermoplastic material to said catheter to result in a hardness of at least 90 on the Shore A scale.

19. The method of claim 12, wherein the step of treating a distal end of said catheter comprises chemically treating the distal end of said catheter.

20. A catheter for insertion into the vascular system of a patient, said catheter having a proximal end and a distal end, said catheter comprising a unitary material and of unitary construction, wherein said integral distal end of said catheter is treated such that said distal end of said catheter is harder than said proximal end of said catheter.

* * * * *